United States Patent [19]

Wagner et al.

[11] Patent Number: 4,634,323

[45] Date of Patent: Jan. 6, 1987

[54] APPARATUS FOR GUIDING WORKPIECES

[75] Inventors: Ralf Wagner, Solingen; Horst Fischer, Hilden; Fritz Heider, Solingen, all of Fed. Rep. of Germany

[73] Assignee: Th. Kieserling & Albrecht, G.m.b.H. & Co., Solingen, Fed. Rep. of Germany

[21] Appl. No.: 545,889

[22] Filed: Oct. 27, 1983

[30] Foreign Application Priority Data

Oct. 29, 1982 [DE] Fed. Rep. of Germany ....... 3240146

[51] Int. Cl.⁴ .............................................. B23B 25/00
[52] U.S. Cl. .................................. 409/167; 51/238 S; 82/38 A; 409/225
[58] Field of Search ............... 409/157, 159, 161, 163, 409/165, 145, 167, 172, 173, 219, 224, 225; 82/38 R, 38 A, 39; 51/103 WH, 103 R, 238 S; 198/721; 414/745; 269/310

[56] References Cited

U.S. PATENT DOCUMENTS

| 3,449,989 | 6/1969 | Bliss | 82/38 R |
| 3,731,566 | 5/1973 | Kurimoto et al. | 51/238 S X |
| 3,839,830 | 10/1974 | Bair | 51/238 S |
| 4,130,035 | 12/1978 | Langley | 82/38 A |
| 4,252,039 | 2/1981 | Wittlen et al. | 82/38 A |
| 4,295,396 | 10/1981 | Hasslauer | 82/38 A X |
| 4,399,639 | 8/1983 | Lesswax | 82/38 R |
| 4,417,491 | 11/1983 | Vehara et al. | 82/38 A |
| 4,516,446 | 5/1985 | Flohn | 82/38 A |
| 4,523,499 | 6/1985 | Alderidge, Sr. | 82/384 X |

FOREIGN PATENT DOCUMENTS

| 2738037 | 3/1979 | Fed. Rep. of Germany | 82/38 A |
| 221920 | 11/1914 | United Kingdom | 51/103 R |

Primary Examiner—Gil Weidenfeld
Assistant Examiner—Glenn L. Webb

[57] ABSTRACT

Apparatus for guiding elongated generally cylindrical workpieces moving longitudinally along an axis includes a plurality of workpiece guides movable toward and away from the axis. An adjustment mechanism selectively moves the workpiece guides toward or away from the axis for positioning such guides in proper guiding relationship to the workpieces. Torsion springs are interposed between the workpiece guides and the adjustment mechanism for allowing yielding movement of the workpiece guides without imparting movement to the adjustment mechanism. Friction dampening devices are provided to inhibit yielding movement of the workpiece guides and to absorb vibrations imparted to the guides by workpieces moving therepast.

18 Claims, 3 Drawing Figures

APPARATUS FOR GUIDING WORKPIECES

BACKGROUND OF THE INVENTION

This application relates to the art of workpiece guide mechanisms and, more particularly, to such mechanisms for guiding elongated generally cylindrical workpieces moving longitudinally along their axes.

Elongated generally cylindrical workpieces such as rods or tubes are commonly guided as they are moved longitudinally into machining, grinding, peeling or straightening devices. Such workpieces commonly have bends or out-of-round eccentric cross-sectional configurations along their length. In view of the bends and eccentricities, it is necessary that the workpiece guides be capable of floating or breathing so that the workpieces will continue to be fed along the same axis throughout their length.

Workpiece guide apparatus of the type described is also subject to severe vibrations which are imparted to the workpieces by the machine tools through which the workpieces are fed and the guide apparatus must absorb these vibrations. Designing a workpiece guide apparatus with a minimum cross-sectional size makes it possible to place the guide apparatus within or very close to the station where work is performed on the workpieces. However, this design reduces the rigidity of the guide apparatus, and increases the distance between workpiece guides and their adjusting means so that the problem of dampening vibrations is magnified.

One known type of workpiece guide apparatus is disclosed in German patent no. 2,156,125 and includes a tubular support body having a passage through which elongated generally cylindrical workpieces move longitudinally along an axis substantially coincidental with the axes of the workpieces. Four spaced-apart shafts are rotatably mounted in the support body parallel to the axis along which the workpieces move. Each shaft has a workpiece guide extending inwardly toward the axis for supporting and guiding the workpieces. The other ends of the shafts have chain wheels connected with a common chain and at least one shaft has an adjusting lever connected with a fluid cylinder. Operation of the cylinder swings the adjusting lever to rotate the shaft and its chain wheel which simultaneously rotates all of the chain wheels and shafts through the common chain. The elastic or yieldable support of the adjusting lever against the fluid cylinder provides a floating or breathing yieldable movement of the workpiece guides. However, all of the workpiece guides will yield in unison with such an arrangement and the workpiece guides can come out of contact with the workpiece. Also, the workpiece guides extend over the entire length of the guide apparatus and workpieces at the entrance or outlet end of the guide apparatus are not always guided at a plurality of spaced locations around their entire circumference. For example, a curved or bent workpiece will be guided at only two or three longitudinally-spaced areas by the workpiece guides. Thus, centering of the workpieces is not assured, and dampening of vibrations in the workpieces is not constantly assured at the outlet end of the guide apparatus.

SUMMARY OF THE INVENTION

In accordance with the present application, a workpiece guide apparatus for guiding elongated generally cylindrical workpieces moving longitudinally along an axis includes workpiece guides. An adjusting means is provided for moving the workpiece guides toward and away from the axis for engaging the workpiece guides with the workpieces in desired supporting and guiding relationship. Torsion springs are interposed between each workpiece guide and the adjusting means for allowing individual yielding movement of each workpiece guide when eccentricities or bends in a workpiece are encountered. This individual yielding movement of the workpiece guides insures that a workpiece will always be engaged at a plurality of circumferentially-spaced areas around its circumference.

In accordance with another aspect of the present application, each workpiece guide includes friction dampening means for inhibiting yielding movement thereof and for dampening the vibrations imparted to the workpiece guides by the workpiece as it is acted upon by machine tools or the like. The workpiece guides are very short in length and are also rigid so that vibrations from the workpieces are transmitted directly through the guides to the vibration dampening means.

The vibration dampening means includes cooperating friction discs and dampening adjustment means is provided for varying the force of engagement between the discs to thereby vary the dampening effects provided.

In a preferred arrangement, the workpiece guides and the adjusting means are located at opposite ends of rotatable shafts which are themselves designed to define the torsion springs which allow yielding movement of each individual workpiece guide without imparting movement to the adjusting means.

Overload release means is provided for the adjusting means so that when the workpiece guides encounter a severe workpiece bend or eccentricity the force transmitted through the torsion springs by yielding movement of the workpiece guides exceeds a predetermined value and operates the overload release means to allow movement of the adjusting means.

The adjusting means includes levers attached to the end portions of the rotatable shafts opposite from the workpiece guides. An adjusting ring rotatably mounted on the support body of the guide apparatus is connected with the levers so that rotation of the adjusting ring swings all of the levers to simultaneously rotate all of the shafts and workpiece guides. A ring adjustment means is provided for selectively rotatably adjusting the adjusting ring and for holding same against rotation in its adjusted position. The overload release means is provided on the ring adjusting means so that operation of the overload release means frees the ring adjusting means so it no longer holds the adjusting ring in its fixed position.

With the arrangement of the present application, extreme bends or eccentricities in a workpiece will not move all of the workpiece guides out of engagement with the workpiece.

It is a principal object of the present invention to provide an improved apparatus for guiding elongated generally cylindrical workpiece moving longitudinally along an axis so that the workpieces are always guided with their axes maintained in a substantially constant location.

It is also an object of the invention to provide an improved workpiece guide apparatus having vibration dampening means for dampening vibrations in each individual workpiece guide to thereby hold and support the workpieces during movement along a substantially constant axis.

It is a further object of the invention to provide a workpiece guide apparatus with workpiece guides which are capable of individual yielding movement in a direction away from the axis and the workpieces without imparting movement to the adjusting means for adjusting the positions of all the workpiece guides.

DESCRIPTION OF A PREFERRED EMBODIMENT

Figure 1:
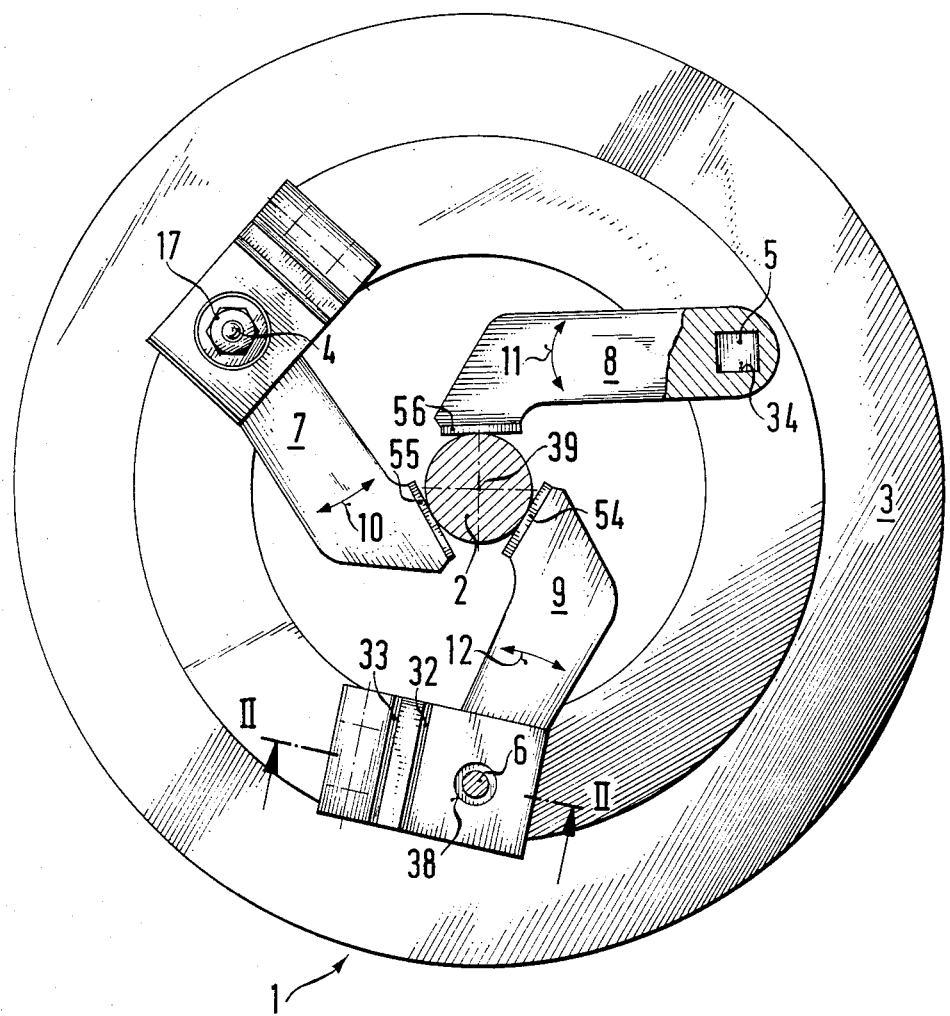
FIG. 1 is an end elevational view of a workpiece guide apparatus constructed in accordance with the present application, and with portions removed and cut-away for clarity of illustration.

Referring now to the drawing, wherein the showings are only for purposes of illustrating a preferred embodiment of the invention and not for purposes of limiting same, FIG. 1 shows a generally cylindrical or tubular support body 3 having a central longitudinal passage through which elongated generally cylindrical workpieces 2, such as rods or tubes, move longitudinally along an axis coinciding with the workpiece axis. Shafts 4,5,6 are rotatably supported in the support body 3 while being fixed against axial movement relative thereto, and are equi-distantly spaced circumferentially from one another outwardly of the central passage through the support body 3. The shafts 4,5,6 also extend substantially parallel to the axis along which the workpieces move.

Workpiece guides or guide arms 7,8,9 are respectively mounted on one end portion of each shaft 4,5,6 against axial or rotational movement relative to such shafts. By way of example, the one end portion of each shaft may be square as generally indicated at 34 in FIG. 1 for shaft 5.

Each workpiece guide 7,8,9 has an end plate 55,56,54 on the inner end portion thereof for engaging the workpiece 2 in supporting and guiding relationship. The guide plates 54, 55,56 extend over a very short length axially of the workpiece axis 39. The guide plates 54,55,56 on the workpiece guides are also beveled or tapered longitudinally so they converge in a direction from the entrance end toward the exit end of the guide apparatus to provide a funnel-like arrangement for a new workpiece moving into the guide apparatus.

Figure 2:
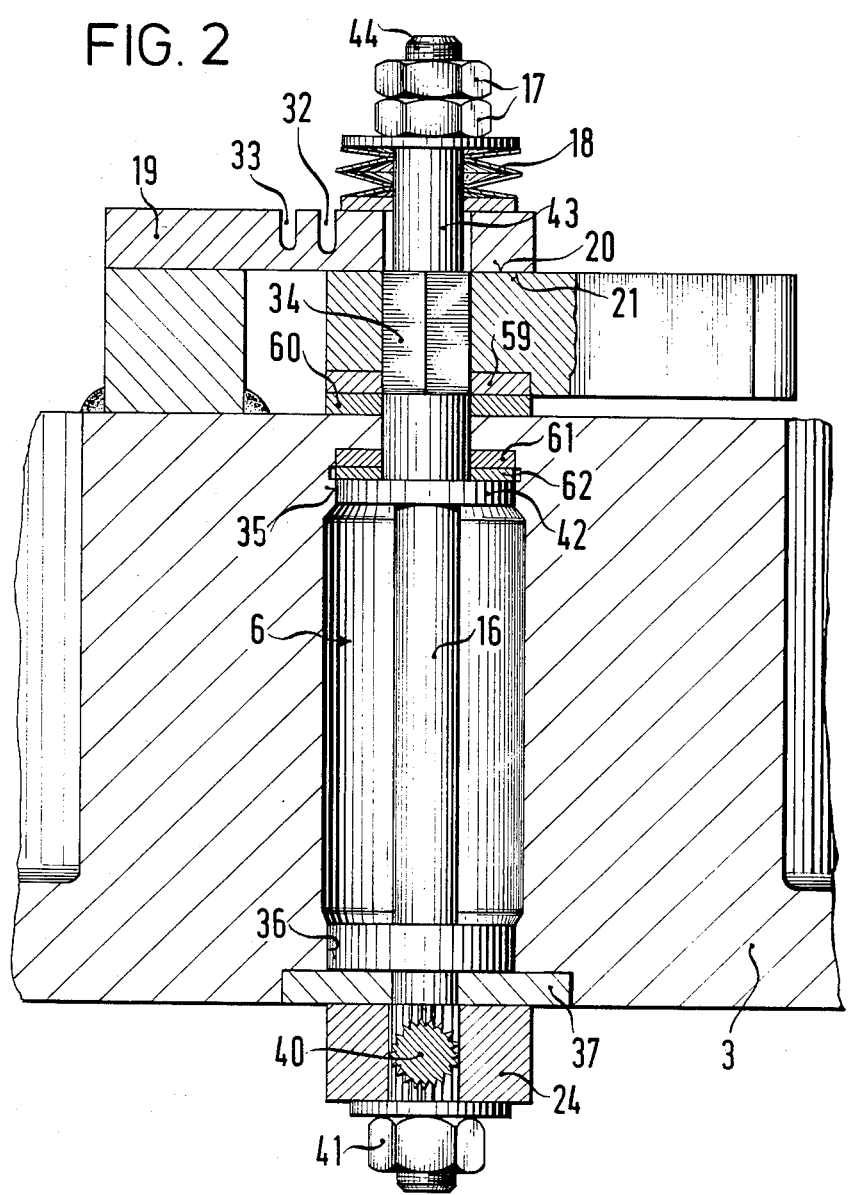
FIG. 2 is a cross-sectional elevational view taken generally on line II—II of FIG. 1.
Figure 3:
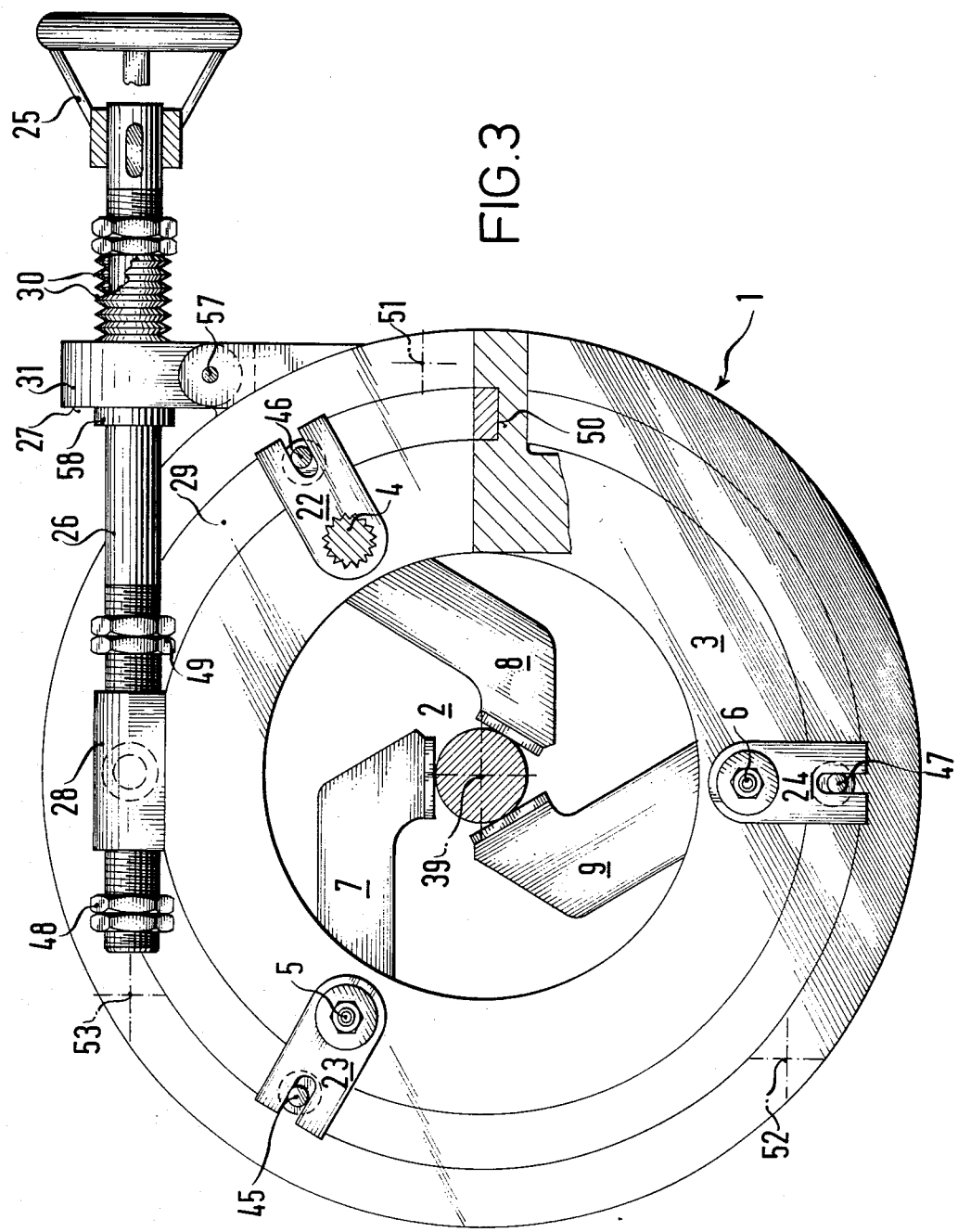
FIG. 3 is a rear end elevational view with portions removed and cut-away for clarity of illustration.

Adjusting means is provided for selectively moving the workpiece guides 7,8,9 toward or away from the axis 39 to properly engage a workpiece in supporting and guiding relationship. As shown in FIG. 3, the adjusting means includes adjusting levers 22,23,24 attached to the opposite ends of the shafts 4,5,6 from the workpiece guides 7,8,9. A rotatable adjusting ring 29 is suitably connected with all of the adjusting levers 22,23,24 so that rotation of the adjusting ring 29 swings the levers simultaneously to rotate the shafts 4,5,6 and thereby simultaneously move the workpiece guides 7,8,9 toward or away from the workpiece. Each shaft 4,5,6 extends between its workpiece guide and its adjusting lever. As shown in FIG. 2, shaft 6 extends between workpiece guide 9 and the adjusting lever 24. A torsion spring is interposed between each workpiece guide and its adjusting lever and, in the arrangement shown in FIG. 2, the torsion spring is generally indicated at 16 as a part of the shaft 6 itself. In other words, each shaft is itself designed as a torsion bar to provide twisting thereof under torsion load. Obviously, other arrangements may be provided for interposing a torsion spring between each guide arm and the adjusting means.

Each shaft and workpiece guide is provided with friction dampening means as will be described with respect to the shaft 6 and the workpiece guide 9 of FIG. 2. Vibration dampeners 20 and 21, 59 and 60, and 61 and 62 are provided for dampening vibrations and inhibiting rotation of the shafts and workpiece guides. Vibration energy imparted to the workpiece guides by vibrations of the workpieces are converted to heat between the friction surfaces of the friction dampening means.

The friction surface 21 is defined by the outer surface on the guide arm itself. The friction surface 20 cooperating with the surface 21 is part of a brake block 19 which is secured to the support body 3 and lies against the surface 21 of the workpiece guide 9. The brake block 19 is slotted twice at 32,33 and that portion of the brake block movable by virtue of the slots is pressed by a spring 18 against the workpiece guide 9 so that complete contact is obtained between the surfaces 20,21. The described arrangement provides friction dampening between each workpiece guide and the support body 3 and also between each shaft and the support body.

The friction discs 59 and 60, and 61 and 62, are designed as replaceable wear parts and are either secured fast to the frame, or to the workpiece guides or shafts. Instead of using replaceable wear parts, a special surface treatment of the surfaces may also be provided.

Dampening adjustment means is provided in the form of the nuts 17 suitably threaded on the outer end portion of each shaft to vary the compressive force in the spring 18 and thereby vary the force of engagement between the various friction surfaces. This makes it possible to vary the dampening characteristics and to vary the degree by which rotation of each shaft and its workpiece guide is inhibited.

Each shaft 4,5,6 has two spaced rotatable bearing points as indicated at 35,36 for the shaft 6 in FIG. 2. The shaft 6 is fixed against axial movement in one direction by a ring 42 in the support body 3 which in turn bears against the friction discs 61,62, and by a support plate 37 attached to the support body 3 in the other direction.

Each adjusting lever 22,23,24 is attached to its corresponding shaft as by a splined connection generally indicated at 40 in FIG. 2. Obviously, many other arrangements may be provided for attaching the adjusting levers to the shafts against axial and rotational movement relative thereto. As shown for the adjusting lever 24 in FIG. 2, each adjusting lever is held to its shaft as by a nut 41 suitably threaded on the shaft.

As previously mentioned, all of the workpiece guides 7,8,9 are simultaneously adjusted by operation of the adjusting means which includes the adjusting ring 29. The support body 3 has an outwardly extending flange at its end portion adjacent the adjusting levers 22,23,24. Thus, the support body 3 has a small diameter end portion adjacent the workpiece guides 7,8,9 and a large diameter end portion adjacent the adjusting levers 22,23,24. A circumferential groove is provided in the end face of the flange on the support body 3 for rotatably receiving the support ring 29. Pins 45,46,47 are attached to the adjusting ring 29 by eccentrics and extend into suitable radial slots in the adjusting levers 22,23,24. Rotation of each eccentric for each pin 45,46,47 makes it possible to individually adjust the position of each adjusting lever and each workpiece guide so that all of the workpiece guides will engage a workpiece with essentially the same support and guiding characteristics.

The adjusting ring 29 is selectively adjusted or rotated by a ring adjusting means which includes a hand wheel 25 and a spindle 26 rotatable by operation of the hand wheel 25. The spindle 26 is supported relative to the support body 3 on a bearing stand 31 attached to the body 3 as by a pivot joint 57. The spindle 26 is connected by an adjustment sleeve 28 to the adjusting ring 29 and the sleeve 28 cooperates with the spindle 26 to move axially therealong upon rotation of the spindle. For example, cooperating threads may be provided between the spindle 26 and the adjustment sleeve 28. The spindle 26 is fixed against axial movement to the right in FIG. 3 by a stop 58 thereon which engages a stop surface 27 on the bearing stand 31. Longitudinal movement of the sleeve 28 on the spindle 26 results in rotation of the adjusting ring 29 and the setting range is limited by end stops 48,49 at opposite ends of the sleeve 28. The pivot connection 57 allows the sleeve 28 and its connection with the adjusting ring 29 to move slightly upwardly or downwardly in FIG. 3 to follow the rotation of the adjusting ring.

Movement of the spindle 26 to the left in FIG. 3 is prevented by overload release means in the form of a spring 30 held by adjustable nuts against the opposite side of the bearing stand 31 from the stop 58. The adjustment nuts for the spring 30 are suitably threaded on the spindle 26. The spring 30 also draws the stop 58 into engagement with the stop surface 27. When the workpiece guides 7,8,9 encounter an extreme bend or eccentricity in a workpiece, the force transmitted from one or more workpiece guides through the torsion springs to the adjusting levers exceeds the predetermined value of the holding force provided by the spring 30 and this force causes swinging of the adjusting levers to rotate the adjusting ring and move the spindle 26 to the left in FIG. 3 against the force of the overload release means 30. In normal operation, the releasing force of the releasing means defined by the spring 30 is greater than the force transmitted through the torsion springs so that the individual workpiece guides 7,8,9 are allowed to move individually by yielding of the torsion springs without imparting any swinging movement to the adjusting levers.

The support body 3 may be attached to a machine tool or the like as by suitable fasteners diagrammatically indicated at 51,52,53 in FIG. 3. The adjusting ring 29 is concentric with the longitudinal axis 39 of the workpiece 2 and rotation of the adjusting ring results in simultaneous swinging movement of all the adjusting levers, shafts and workpiece guides. Thus, each workpiece 2 is always centrally guided and the position of each workpiece longitudinal axis remains substantially unchanged when the workpiece guides are adjusted for guiding workpieces of different diameters.

Most of the vibrations and yielding movements for each individual workpiece guide 7,8,9 are taken up by the friction dampening means and the torsion springs, and only the excess force is transmitted to the adjusting levers. It is only when the excess force on the adjusting levers exceeds the holding force of the spring 30 on the spindle 26 that all of the workpiece guides will move outwardly away from a workpiece. This means that an individual workpiece guide will lift completely off from a workpiece only when there is an extreme deviation in the shape of a workpiece. That is, only when the sum of all the forces transmitted by all of the torsion springs 16 to the adjusting levers exceeds the prestressed value set on the overload release means 30 is it possible for a workpiece guide to move completely out of engagement with the workpiece. Also, individual vibrations of each workpiece guide are taken up by the individual dampening arrangements for each shaft and workpiece guide without having any influence on the other workpiece guides. The force on the spring 18 in FIG. 2 for the dampeners can be adjusted along with the force of the spring 30 on the spindle 26. This makes it possible to fine tune the guide apparatus to the desired threshhold load which is required to release the overload safety device. By guiding only a very short length of each workpiece by the guides, bends in the workpieces have little or no influence on the dampening characteristics of the apparatus.

The elastic design of each shaft as a torsion spring as indicated at 16 in FIG. 2 makes it possible to reduce the transverse size of not only the shafts but also the wall thickness of the support body 3 and the entire guide apparatus. This makes it possible to provide a larger passage through the support body and the range of diameters of workpieces which can be guided is substantially increased.

Although a preferred embodiment of the present invention has been shown in the drawing and described in the specification, it is obvious that equivalent alterations and modifications will occur to others skilled in the art upon the reading and understanding of this specification. The present application includes all such equivalent alterations and modifications, and is limited only by the scope of the claims.

What is claimed is:

1. Apparatus for guiding elongated workpieces moving longitudinally along an axis comprising: a plurality of spaced workpiece guides movable toward and away from said axis, guide adjusting means for selectively moving said guides toward and away from said axis, a torsion spring interposed between each said guide and said adjusting means for providing yielding movement of said guides relative to said adjusting means, and wherein said guides and guide adjusting means are connected by shafts extending generally parallel to said axis and at least a portion of each said shaft defines said torsion spring.

2. The apparatus according to claim 1 and vibration dampening means between each said guides and each said torsion springs.

3. The apparatus according to claim 2 wherein said vibration dampening means includes at least one friction disc.

4. The apparatus of claim 1 wherein said guide adjusting means includes overload release means for providing movement of said guide adjusting means responsive to yielding movement of said guides when the force transmitted through said torsion springs from said guides to said guide adjusting means exceeds a predetermined value.

5. The apparatus of claim 4 including overload release adjusting means for varying the force required to operate said overload release means.

6. The apparatus of claim 1 including vibration dampening means for inhibiting yielding movement of said guides.

7. The apparatus of claim 6 including dampening adjustment means for varying the inhibiting action of said dampening means on said guides.

8. Apparatus for guiding elongated workpieces moving longitudinally along an axis comprising: a plurality of spaced workpiece guides movable toward and away from said axis, guide adjusting means for selectively moving said guides toward and away from said axis, and a torsion spring interposed between each said guide and said adjusting means for providing yielding movement of said guides relative to said adjusting means, support means for said guides and guide adjusting means, said support means including a generally cylindrical support body having an outwardly extending flange at one end portion thereof so that said body has a small diameter end portion and an opposite large diameter end portion, said support body having a workpiece passage therethrough between said end portions, said guides being mounted adjacent said small diameter end portion and said adjusting means being mounted adjacent said large diameter end portion, a plurality of shafts extending rotatably through said body generally parallel to the longitudinal axis of said workpiece passage, said guides being attached to first end portions of said shafts and said adjusting means being cooperable with opposite end portions of said shafts, and at least portions of said shafts defining said torsion springs.

9. Apparatus according to claim 8 including vibration dampening means between each said guides and each said torsion springs.

10. The apparatus of claim 8 wherein said guide adjusting means includes levers attached to said opposite end portions of said shafts, an adjusting ring rotatably attached to said large diameter end portion of said support body, connecting means for connecting said ring with said levers, whereby rotation of said adjusting ring relative to said support body simultaneously swings said levers to rotate said shafts and move said workpiece guides.

11. Apparatus for guiding elongated cylindrical workpieces moving longitudinally along an axis comprising: a support body having a workpiece passage therethrough, a plurality of spaced shafts extending rotatably through said body generally parallel to the longitudinal axis of said passage, workpiece guides attached to first end portions of said shafts at one end of said body for movement toward or away from said longitudinal axis responsive to rotation of said shafts, adjusting levers attached to opposite end portions of said shafts at the opposite end of said body, lever adjusting means for swinging said levers to rotate said shafts and selectively move said guides toward or away from said axis, and torsion spring means interposed between each said guide and lever for providing yielding movement of said guides away from said axis without imparting movement to said levers.

12. The apparatus according to claim 11 including vibration dampening means between each said guides and each said torsion springs.

13. The apparatus according to claim 11 including vibration adjustment means for varying the inhibiting action of said dampening means on said guides.

14. The apparatus of claim 11 including friction dampening means for inhibiting yielding movement of said guides.

15. The apparatus of claim 11 wherein said torsion spring means comprises at least a portion of each said shaft.

16. The apparatus of claim 11 including overload release means for providing movement of said levers when the force imparted thereto through said spring means by yielding movement of said guides exceeds a predetermined value.

17. The apparatus of claim 11 wherein said support body includes an outwardly extending flange at one end portion thereof and includes a flange end face, said lever adjusting means including an adjusting ring rotatably mounted in a circular groove in said flange end face, connecting means for connecting said adjusting ring to said levers, and ring adjusting means for selectively rotating said ring to simultaneously swing all said levers to rotate said shafts and move said guides inwardly or outwardly relative to said axis.

18. The apparatus of claim 17 wherein said ring adjusting means holds said ring against rotation in its adjusted position, and overload release means for releasing said ring adjusting means to provide rotation of said ring when the force imparted thereto from yielding movement of said guides through said spring means and levers exceeds a predetermined value.

* * * * *